US008748472B2

(12) United States Patent
Chang et al.

(10) Patent No.: US 8,748,472 B2
(45) Date of Patent: Jun. 10, 2014

(54) STABILIZED FORMULATIONS OF CNS COMPOUNDS

(75) Inventors: Rong-Kun Chang, Rockville, MD (US); Michael L. Vieira, Gaithersburg, MD (US); Likan Liang, Boyds, MD (US); Padmanabh P. Bhatt, Rockville, MD (US); Austin B. Huang, N. Potomac, MD (US); Sachin V. Patel, Derwood, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 117 days.

(21) Appl. No.: 13/075,607

(22) Filed: Mar. 30, 2011

(65) Prior Publication Data

US 2011/0244042 A1 Oct. 6, 2011

Related U.S. Application Data

(60) Provisional application No. 61/282,787, filed on Mar. 31, 2010.

(51) Int. Cl.
*A61K 31/40* (2006.01)

(52) U.S. Cl.
USPC ............................ 514/411; 424/457; 424/468

(58) Field of Classification Search
USPC .................................. 424/457, 468; 514/411
See application file for complete search history.

(56) References Cited

U.S. PATENT DOCUMENTS

| 4,148,896 A | * | 4/1979 | Smith et al. ................. 514/235.2 |
| 5,202,128 A | * | 4/1993 | Morella et al. ................. 424/469 |
| 2002/0156078 A1 | * | 10/2002 | Comings et al. ........... 514/233.5 |
| 2009/0004229 A1 | | 1/2009 | Pastini et al. | |
| 2010/0173907 A1 | | 7/2010 | Breder | |

FOREIGN PATENT DOCUMENTS

| GB | 2447949 A | 10/2008 |
| WO | WO 2004/106298 A1 | 12/2004 |
| WO | WO 2005/121113 A1 | 12/2005 |

OTHER PUBLICATIONS

Greenhill et al., "Molindone Hydrochloride Treatment of Hospitalized Children with Conduct Disorder," J. Clin. Psychiatry, Aug. 1985, 46(8:Sec.2):20-25.
Findling, Robert L., M.D., "Treatment of Aggression in Children," Primary Care Companion J. Clin. Psychiatry, 2003, 5(Supp6):5-9.
International Search Report and Written Opinion mailed May 23, 2011, in corresponding PCT/US2011/30444, 8 pages.
Bagnall et al,. "Molindone for schizophremia and severe mental illness (Review)," Cochrane Database Syst. Rev., 2007(1):CD002083, 62 pages.
Findling et al., "Effectiveness, Safety, and Pharmacokinetics of Quetiapine in Aggressive Children with Conduct Disorder," J. Am. Acad. Child Adolesc. Psychiatry, Jul. 2006, 45(7):792-800.
Greenhill et al., "Molindone Hydrochloride in the Treatment of Aggressive, Hospitalized Children," Psychopharmacol. Bull., Jan. 1981, 17(1):125-127.
Hartman et al., "Molecular Attributes of Dopamine Receptors: New Potential for Antipsychotic Drug Development," Ann. Med., 1996, 28:211-219.
Holmes et al., "Behavioral Characterization of Dopamine D5 Receptor Null Mutant Mice," Behavioral Neuroscience, 2001, 115(5):1129-1144.
Itil et al., "Treatment of Human Aggression with Major Tranquilizers, Antidepressants, and Newer Psychotropic Drugs," The Journal of Nervous and Mental Disease, 1975, 160(2):83-99.
Jensen et al., "Consensus Report on Impulsive Aggression as a Symptom Across Diagnostic Categories in Child Psychiatry: Implications for Medication Studies," J. Am. Acad. Child Adolesc. Psychiatry, Mar. 2007, 46(3):309-321.
Maher et al. "Dopamine system genes and attention deficit hyperactivity disorder: a meta-analysis," Psychiatric Genetics, 2002, 12(4):207-215.
Matsumoto et al,. "Neurons in the Thalamic CM-Pf Complex Supply Striatal Neurons with Information About Behaviorally Significant Sensory Events," J. Neurophysiol., 2001, 85(2):960-976.
McClellan et al., "Treatment of Early-Onset Schizophremia Spectrum Disorders (TEOSS): Rationale, Design, and Methods," J. Am. Acad. Child Adolesc. Psychiatry, Aug. 2007, 46(8):969-978.
Sikich et al., "Double-Blind Comparison of First- and Second-Generation Antipsychotics in Early-Onset Schizophrenia and Schizoaffective Disorder: Findings From the Treatment of Early-Onset Schizophremia Spectrum Disorders (TEOSS) Study," Am. J. Psychiatry, Nov. 2008, 165(11)1420-1431.
Vanyukov et al., "Antisociality, Substance Dependence, and the *DRD5* Gene: A Preliminary Study," American Journal of Medical Genetics (Neuropsychiatric Genetics), 2000, 96(5):654-658.
Jordan et al., "The Antipsychotic Aripiprazole is a Potent, Partial Agonist at the Human 5-HT1A Receptor," European Journal of Pharmacology, 2002, 441:137-140.
Claustre et al., SSR181507, A Dopamine D2 Receptor Antagonist and 5-HT1A Receptor Agonist. I: Neurochemical and Electrophysiological Profile, 2003, Neuropsychopharmacology, 2003, 28:2064-2076.

* cited by examiner

*Primary Examiner* — Ali Soroush
(74) *Attorney, Agent, or Firm* — Foley & Lardner LLP

(57) ABSTRACT

Formulations of molindone having superior stability and methods of administering same are provided. The formulations may be immediate, modified, or otherwise delayed release formulations of molindone.

44 Claims, 9 Drawing Sheets

Fig. 1. Molindone HCl solubility profile at ambient conditions
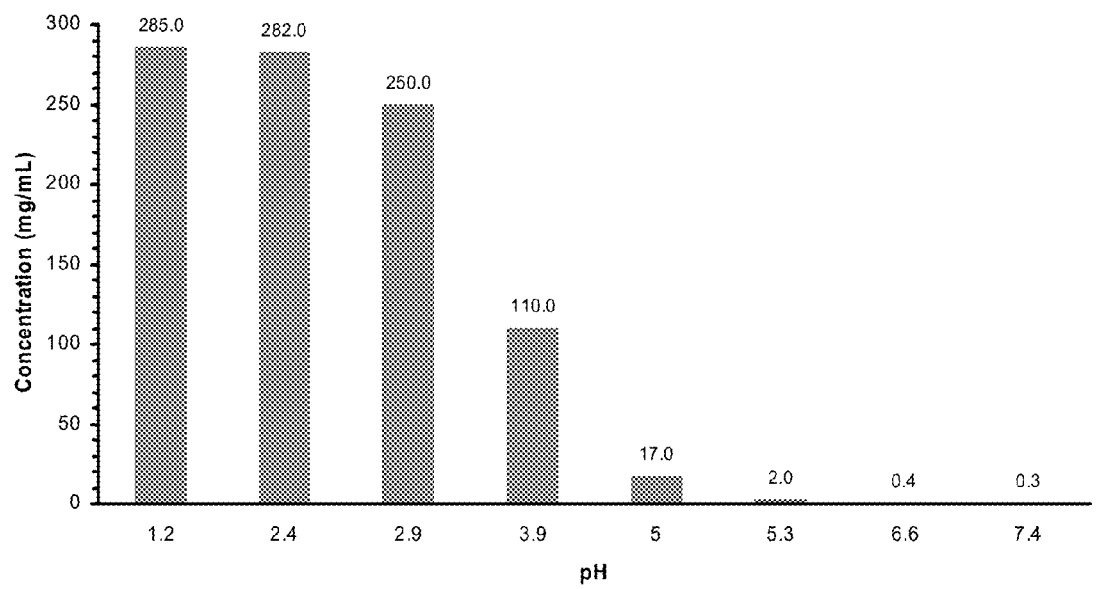

Fig. 2. Mean *In-vitro* Molindone Dissolution Profiles
Matching dissolution profiles for tablets dose strengths ranging from 3mg to 72mg
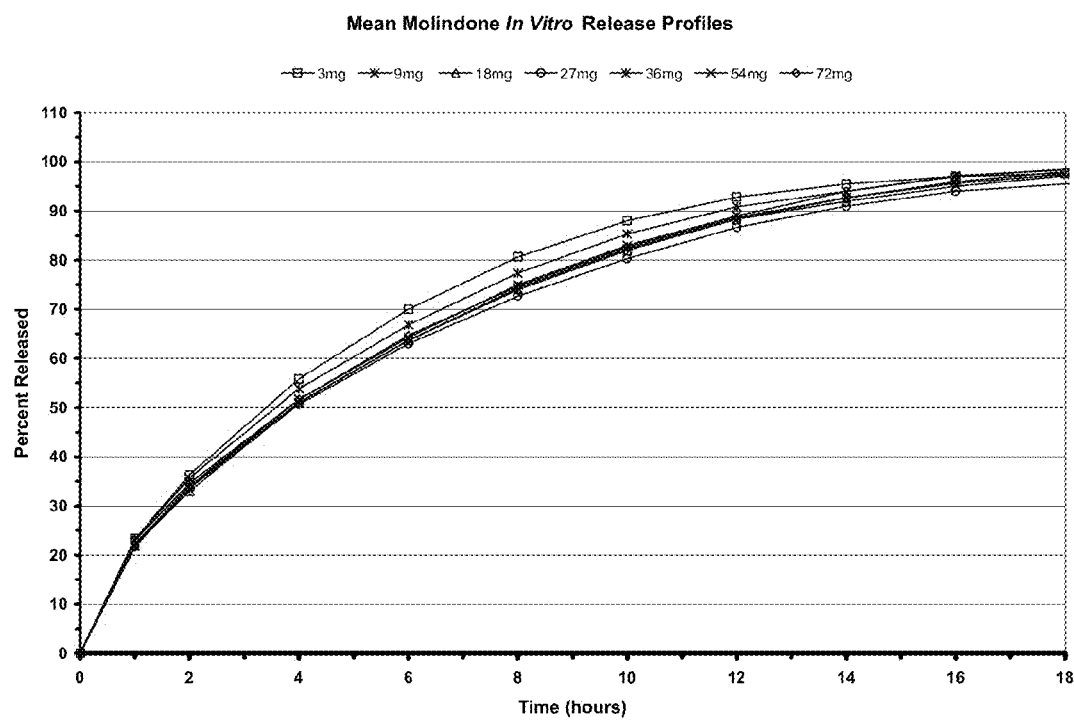

Fig. 3. Fasted state plasma profiles for the immediate release formulation of molindone and three modified release formulations
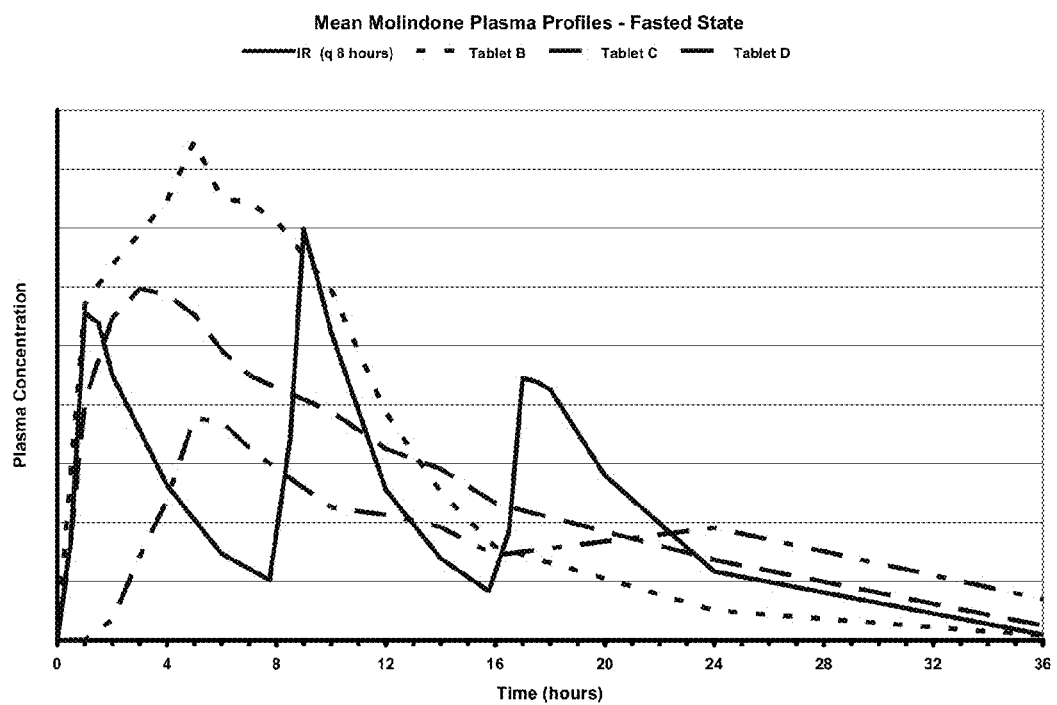

Fig. 4. Simulated Steady State Plasma Profiles of Molindone Tablets B, C and D Dosed Once Daily
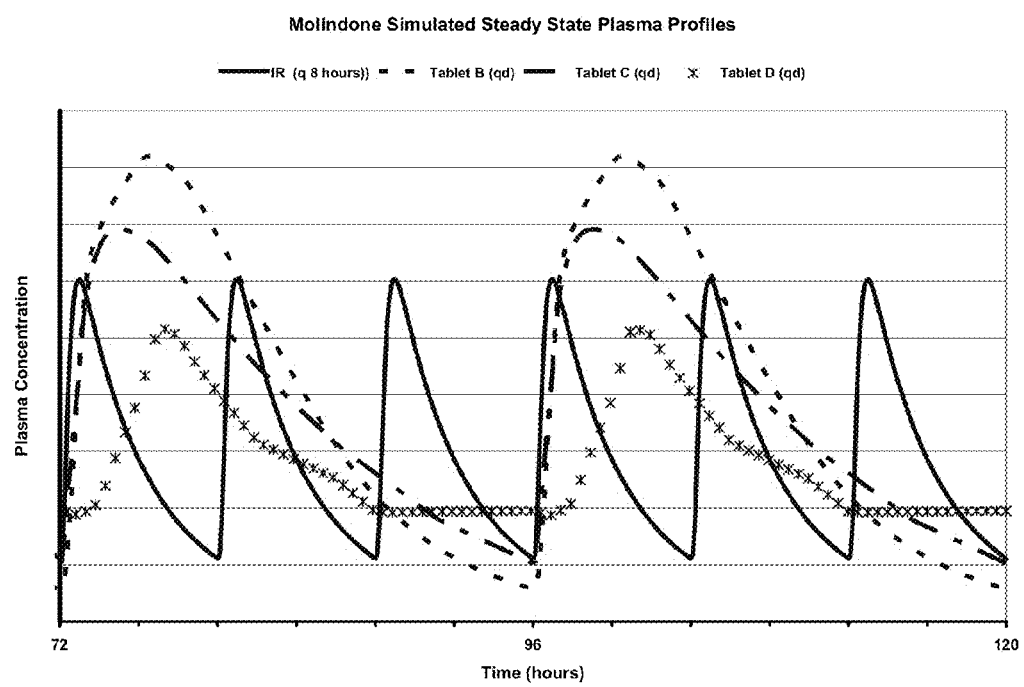

Fig. 5. Simulated Steady State Plasma Profiles of Molindone Tablet B Dosed Twice Daily
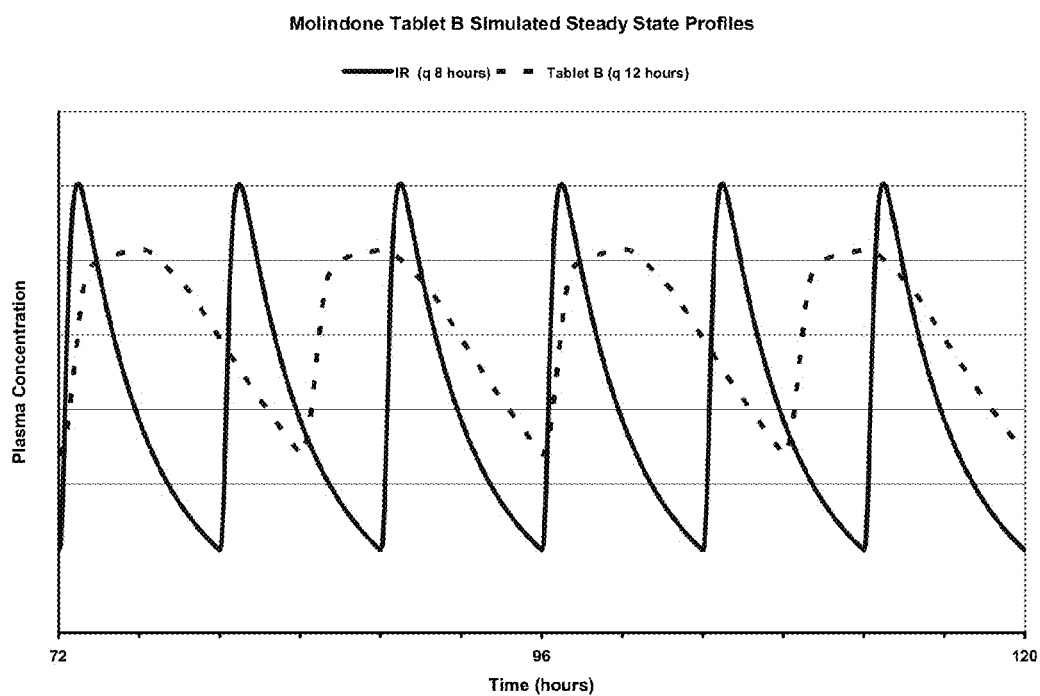

Fig. 6. Simulated Steady State Plasma Profiles of Molindone Tablet C Dosed Twice Daily
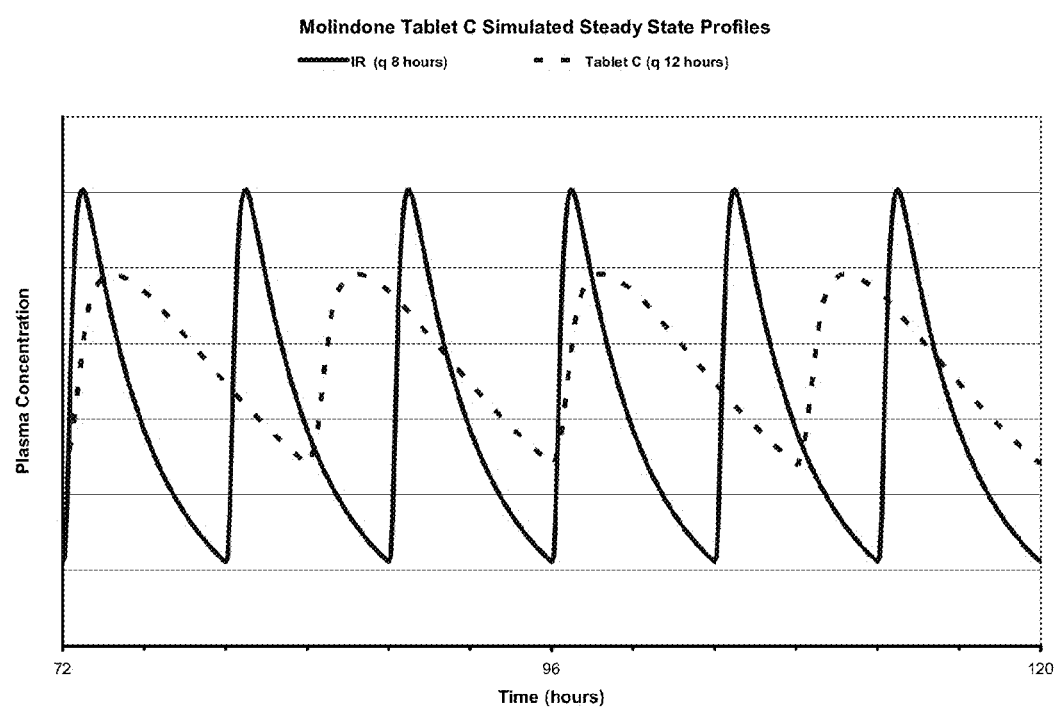

Fig. 7. Pilot dose linearity PK study in 15 healthy subjects
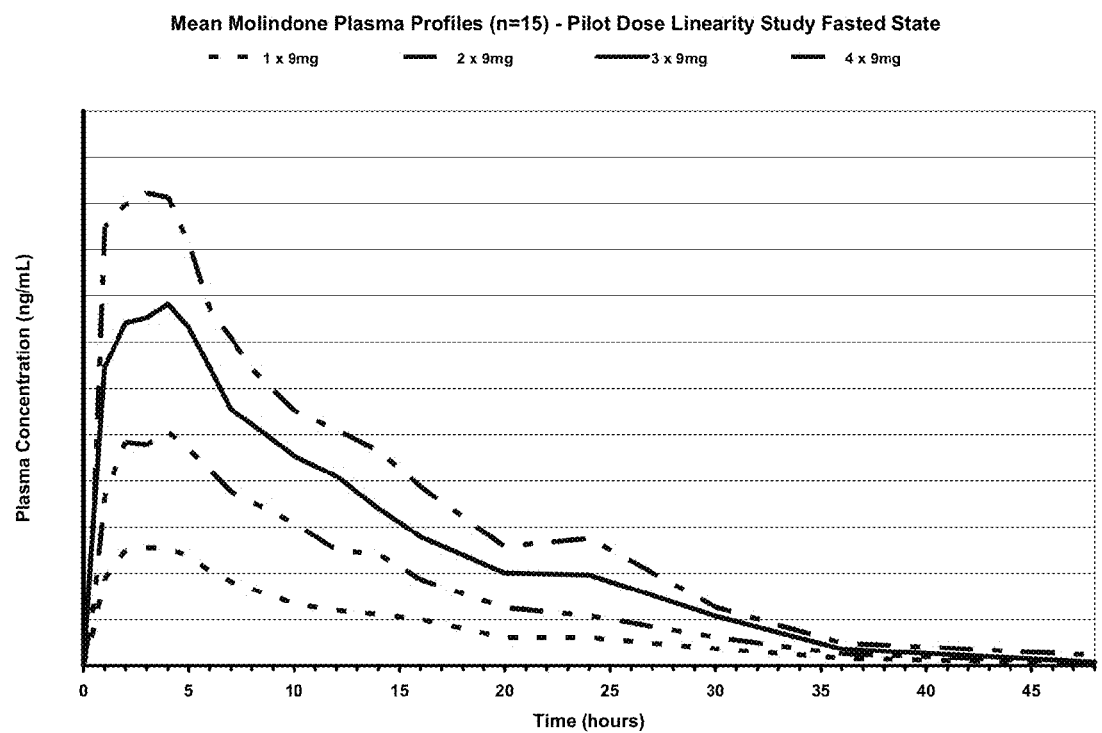

Fig. 8. Pilot drug product proportionality PK study in healthy subjects
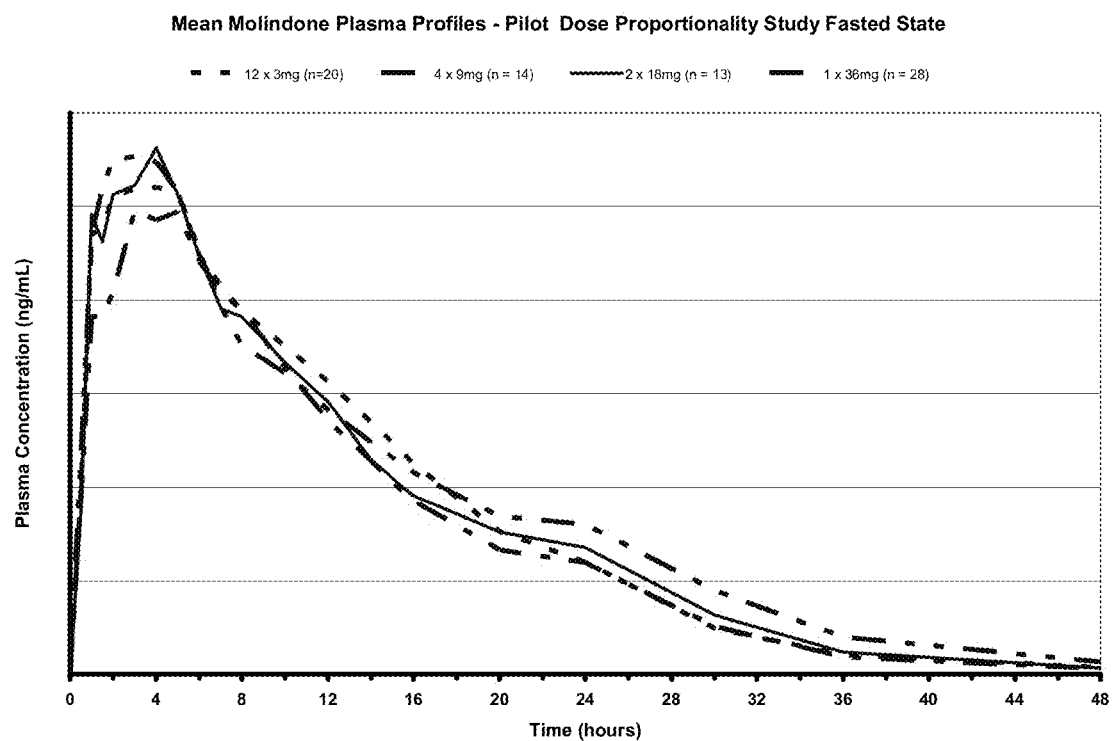

Fig. 9. Pilot drug product linearity PK study in healthy subjects
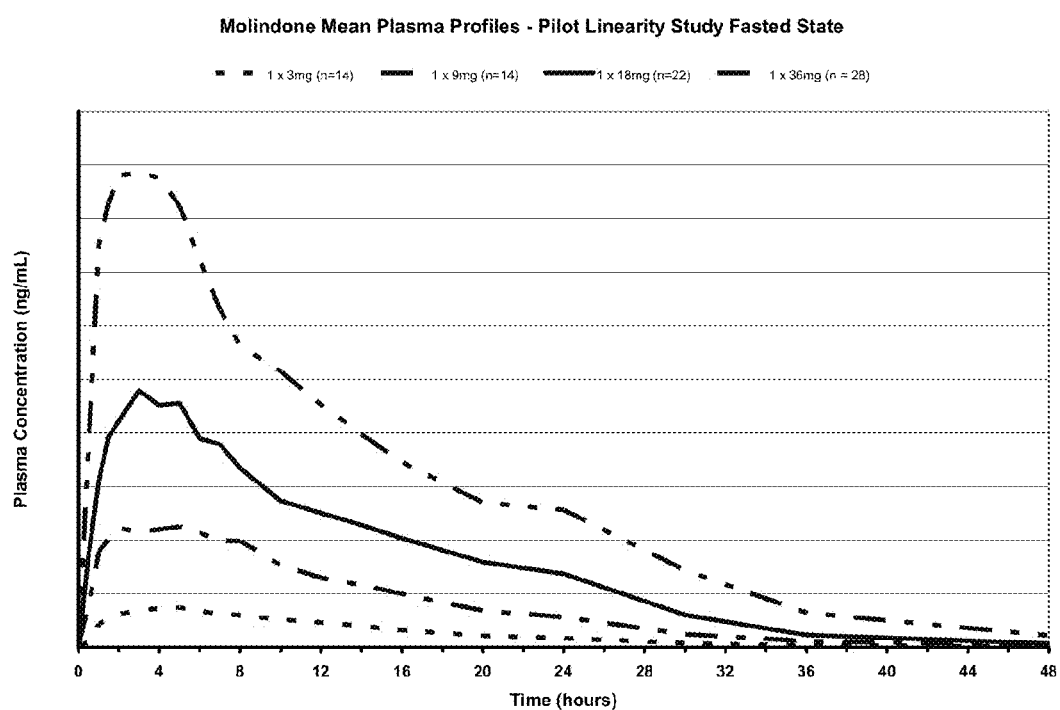

STABILIZED FORMULATIONS OF CNS COMPOUNDS

CROSS-REFERENCE TO RELATED APPLICATIONS

This application claims priority to U.S. Provisional Application No. 61/282,787, filed Mar. 31, 2010.

FIELD OF THE INVENTION

The current invention is directed towards stabilized formulations of molindone, 3-Ethyl-6,7-dihydro-2-methyl-5-(morpholinomethyl)indol-4(5H)-one (CAS #7416-34-4). The structure of molindone is represented below:

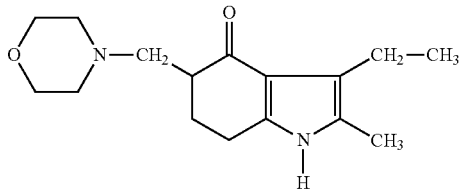 [SMILES: CCc1c(C)[nH]c2c1C(=O)C(CN1CCOCC1)CC2]

BACKGROUND OF THE INVENTION

Molindone is a weak base, exhibiting greater solubility (FIG. 1) in acidic to slightly acidic media than in neutral to slightly alkaline pH values (i.e., the physiologic pH range of the gastro-intestinal tract). As a weakly basic drug, molindone is typically included into formulations in the form of a salt, such as chloride, sulfate, phosphate, monohydrogenphosphate, dihydrogenphosphate, bromide, iodide, acetate, propionate, decanoate, caprylate, formate, oxalate, malonate, succinate, fumarate, maleate, citrate, lactate, tartrate, methanesulfonate, mandelate, and the like.

Molindone hydrochloride, a medium potency antipsychotic, was marketed as Moban® for the management of schizophrenia in adults. Moban is an immediate release (IR) tablet formulation provided at the dose strengths of 5 mg, 10 mg 25 mg, 50 mg and 100 mg. As an IR dosage form it is taken 3 to 4 times daily with a typical maintenance dose range of 50 mg-100 mg per day. Limited molindone pharmacokinetic (PK) data is available in the literature. The drug substance has a reported bioavailability of 60%-70% relative to an intramuscular (IM) dose. It is absorbed rapidly following oral administration with a $t_{max}$ observed between 1 to 1.5 hours. The drug substance is extensively and rapidly metabolized with an oral dose plasma elimination half-life of about 2 hours.

SUMMARY OF THE INVENTION

One embodiment of the current invention is directed towards stable IR and modified release (MR) formulations of molindone that comprise not more than 5% by weight of the formulation of water. Further, the modified release formulations comprising stabilizing agents are also disclosed. In one embodiment of the invention, the MR formulation is an extended release (XR) formulation. In another embodiment, the MR formulation is a delayed release (DR) formulation. In yet further embodiment, the MR formulation is a formulation that provides a pulsatile release. The pulsatile release may be achieved using a combination of an XR with a DR, or an IR with an XR, or an IR with a DR, or an IR with an XR and DR.

In another embodiment of the invention, stable IR formulations of molindone that comprise not more than 5% by weight of the formulation of water are provided. In yet further embodiment, the invention discloses stabilized IR formulations of molindone comprising stabilizing agents.

A further embodiment covers a dosage form containing the formulation of the current invention wherein said dosage form is selected from tablets, mini tablets, capsules, beads, granules, powders, caplets, troches, sachets, cachets, pouches, gums, sprinkles, solutions, suspensions, and buccal and gastro-retentive preparations. The tablets may be osmotic tablets, matrix tablets, bi- and multilayer tablets, fast disintegrating tablets and other type of tablets commonly used in the art. The formulation may be also presented in the form of pellets in a capsule, where the capsule may be swallowed whole or can be opened and the pellets sprinkled on to soft food or in a liquid and then swallowed.

Further, the present invention provides a once-a-day dosage form of molindone delivering to a mammal from 0.1 mg to 200 mg of molindone for the treatment of CNS disorders, including but not limited to the treatment of impulsive aggression, aggression, or other conduct disorder. In an additional embodiment, it also provides a once-a-day dosage form that can provide treatment of CNS disorders, including but not limited to impulsive aggression, aggression, or other conduct disorder. In a further embodiment, the invention provides a formulation that provides a therapeutically effective blood concentration of molindone for the period of time from 4 to 24 hours, preferably from 6 to 24 hours, more preferably from 8 to 24 hours.

BRIEF DESCRIPTION OF THE DRAWINGS

FIG. 1 shows the molindone hydrochloride solubility profile at ambient conditions.

FIG. 2 shows in-vitro mean molindone dissolution profiles.

FIG. 3 shows fasted state plasma profiles for the IR formulation of molindone and three MR formulations.

FIG. 4 shows simulated steady state plasma profiles of molindone for the IR formulation of molindone dosed three times daily and three MR formulations dosed once daily.

FIG. 5 shows simulated steady state plasma profiles of molindone for the IR formulation of molindone dosed three times daily and Tablet B dosed twice daily.

FIG. 6 shows simulated steady state plasma profiles of molindone for the IR formulation of molindone dosed three times daily and Tablet C dosed twice daily.

FIG. 7 shows results of a pilot dose linearity PK study in 15 healthy subjects.

FIG. 8 shows results of a pilot drug product proportionality PK study in healthy subjects.

FIG. 9 shows results of a pilot drug product linearity PK study in healthy subjects.

DEFINITIONS

Unless otherwise specified, "a" or "an" means "one or more".

The term "molindone" means 3-Ethyl-6,7-dihydro-2-methyl-5-(morpholinomethyl)indol-4(5H)-one or a pharmaceutically acceptable salt or ester thereof, including either a single (−) enantiomer, or in the form of a single (+) enantiomer, or in the form of a racemic mixture of both, or in the form of a non-racemic mixture of enantiomers with varying amounts of (−) and (+) enantiomers. An "immediate release formulation" refers to a formulation that releases greater than or equal to about 80% by weight of the pharmaceutical agent in less than or equal to about 1 hour.

The term "modified release" encompasses any mode of release that is different from the immediate release.

In the current application, the term "non-pH dependent polymers" is used to mean "polymers having solubility that is not pH-dependent" and a term "pH-dependent polymers" is used to mean "polymers having solubility that is pH-dependent";

For the purposes of this application, terms "pH-dependent polymers" and "enteric polymers" are used interchangeably.

The term "particles", as used herein, includes, without any limitations on the nature and size thereof, any particles, spheres, beads, granules, pellets, particulates or any structural units that may be incorporated into an oral dosage form.

DETAILED DESCRIPTION OF THE INVENTION

Though molindone salts are chemically stable in the solid state, creating stable IR or MR formulations of molindone presents a significant challenge because it appears that molindone salts, for example molindone hydrochloride, are not compatible with many commonly used pharmaceutical excipients. Combination of molindone with these excipients to produce a dosage form results in significant degradation of the active agent.

It was unexpectedly discovered that the problem of molindone's instability in the presence of excipients may be solved by keeping the total amount of the water in the formulation to a very low level, less than 5% by weight of the formulation, preferably less than 2% by weight of the formulation.

It was further discovered that stable IR and MR formulations of molindone may be prepared with the use of certain excipients (hereinafter referred to as "stabilizing excipients"). In one embodiment of the invention, the stabilizing excipients are acidifiers selected from the group consisting of fumaric acid, citric acid, malic acid, tartaric acid, ascorbic acid, edetic acid, aspartic acid, adipic acid, alginic acid, benzoic acid, butandioic acid, erythorbic acid, lactic acid, malic acid, maleic acid, glutamic acid, sorbic acid, succinic acid, hydrochloric acid (dilute) nitric acid (dilute), phosphoric acid (dilute), sulfuric acid (dilute), acacia, aluminum phosphate, aluminum sulfate, ammonium alum, ammonium chloride, carbomers, edetate calcium disodium, edetate disodium, methacrylic acid copolymers, poly(methyl acrylate-comethyl methacrylate-co-methacrylic acid), polycarbophils, polydextrose, potassium alum, potassium phosphate monobasic, sodium metabisulfite, sodium phosphate monobasic, sodium starch glycolate, zinc acetate, zinc sulfate and pharmaceutical grade ion exchange resins (such as Amberlite IRP64, Amberlite IRP69 and Amberlite IRP88) among others.

In another embodiment of the invention, stabilizing excipients are selected from hydrophobicity inducing agents. These agents may be represented by magnesium stearate, stearic acid, glyceryl stearate, glyceryl palmitostearate, stearoyl macrogolglycerides, lauroyl macrogolglycerides, waxes and hydrogenated vegetable oils, among others.

The stabilizers may be included into the formulations of the current invention in the amount such that, for an individual stabilizer, the ratio of the parts by weight of stabilizer to parts by weight of the drug substance is from 0.1:1 to 50:1, preferably from 0.25:1 to 40:1; most preferably from 0.4:1 to 25:1. Combinations of stabilizing excipients may be used in all embodiments of the instant invention and may provide synergistic stabilizing action.

Stabilizers may be incorporated into formulations of molindone in a variety of ways. They may be intermixed with the drug substance and/or other excipients, or may be provided in the form of a coating on the molindone-containing substrate. Water-based acidifiers may be used in the preparation of the formulations of the current invention as long as care is taken to eliminate or reduce water during the processing. Alternatively, excipients, such as bulking agents, may be pre-treated by the stabilizers prior to their incorporation into the formulation. Stabilization of molindone may be also achieved by coating drug layered substrates with coating polymers dissolved or dispersed in acidic solution. These and further ways of using stabilizers are disclosed in more detail in the examples below.

Additional excipients that can be used alone or in combination to formulate stable molindone drug products in accordance with the current invention include bulking agents, such as lactose anhydrous or lactose monohydrate, (i.e., Supertab 21AN, Ludipress, Ludipress LCE, Fast Flo Lactose, Supertose, Pharmatose, Respitose), glyceryl behenate, hypromellose, ascorbic acid, benzoic acid, carbomer, low moisture microcrystalline cellulose (Avicel® grades PH-103, PH-112, PH-113, PH-200), colloidal silicon dioxide, dextrates (anhydrous), dextrose (anhydrous), maltol, fructose, glyceryl palmitostearate, glyceryl monostearate, guar gum, lactilol (anhydrous), magnesium carbonate, maltitol, maltose, mannitol, polyethylene oxide, sorbitol, sucrose, compressible sugar, confectioner's sugar, xylitol; glidants such as talc, starch and colloidal silicon dioxide and the metallic stearates; lubricants selected from talc, sodium stearyl fumarate, hydrogenated vegetable oils, glyceryl palmitostearate, glyceryl behenate, poloxamer, stearic acid, stearyl alcohol, cetyl alcohol, waxes, and the metallic stearates; wetting and solubility enhancing agents, such as sodium lauryl sulfate, polyethylene glycol, PEG glyceryl esters, lecithin, poloxamer, the polysorbates, the polyoxyethylene alkyl ethers, polyethylene castor oil derivatives, polyethylene stearate, and the sorbitan esters.

Through the use of stabilizers and low levels of moisture as described above, the inventors were able to realize one goal of the current invention: to provide stable IR formulations of molindone that comprise not more than 5% of water. In yet further embodiment, the invention discloses stable IR formulations of molindone comprising stabilizing excipients.

A further goal of the current invention is to utilize stabilization techniques described herein to provide stable MR formulations of molindone comprising molindone, at least one release controlling polymer that may be a non-pH-dependent polymer or a pH-dependent, enteric polymer, and at least one pharmaceutically acceptable excipient. Further, the invention provides MR formulations of molindone comprising molindone, at least one release controlling polymer and at least one pharmaceutically acceptable excipient, wherein the total amount of residual water in the formulation is not more than 5% by weight of the formulation.

The MR formulations of molindone exhibiting XR profile, or combination of XR and DR profile, or any combination of those with IR profile are disclosed herein. These specific release profiles are achieved by formulating molindone, at least one release controlling polymer and one or more excipient in a variety of inventive formulations.

The release controlling polymers of the current invention may be selected from non-pH-dependent polymers such as hydrophilic rate controlling compounds that can be used to formulate MR multiparticulates or matrix tablets drug products, and hydrophobic rate controlling compounds that exhibit limited or no water solubility; or enteric polymers that exhibit pH-dependent solubility. The following non-limiting examples of such compounds are provided below:

Hydrophilic compounds: hydroxypropyl cellulose, hypromellose (hydroxypropyl methyl cellulose), methyl cellulose, polyethylene oxide, acacia, acrylic acid derivatives (e.g., carbomer homopolymer type A NF and carbomer homopolymer type B NF), hydroxyethyl cellulose, carrageenan, tragacanth, xanthan gum, povidone, alginic acid (and salts thereof), poly vinyl alcohol, carboxymethylcellulose, and combinations thereof.

Hydrophobic compounds: ethylcellulose, cellulose acetate, cellulose acetate butyrate, waxes (e.g., carnauba wax, microcrystalline wax), hydrogenated vegetable oils, Compritol 888 ATO (glyceryl behenate), Precirol ATO 5 (glyceryl palmitostearate), PEG glyceryl esters such as Gelucire 50/1, Eudragit® NE 30 D or Eudragit NM 30 D poly(ethyl acrylate-co-methyl methacrylate) ethyl acrylate methyl methacrylate copolymer, Eudragit® RS and Eudragit® RL poly(ethyl acrylate-co-methyl methacrylate-cotrimethylammonioethyl methacrylate chloride), polyvinyl acetate, cellulose acetate propionate, and combinations thereof.

Enteric compounds: Eudragit® FS 30 D (poly(methyl acrylate-co-methyl methacrylate-co-methacrylic acid)), Eudragit® L and Eudragit® S (poly(methacrylic acid-co-methyl methacrylate)), Eudragit® L 100-55 (methacrylic acid-ethyl acrylate copolymer), Eudragit® L 30 D-55 (methacrylic acid-ethyl acrylate copolymer dispersion), hydroxypropyl methylcellulose acetate succinate, hydroxypropyl methylcellulose phthalate, cellulose acetate phthalate, shellac, zein, and combinations thereof.

The release controlling polymers (non-pH-dependent polymer, pH-dependent polymer or combination of both) may be included into the formulation in the amount of from 5% to 95% by weight of the formulation, preferably in the amount of from 20% to 85% by weight of the formulation, most preferably in the amount of from 30% to 75% by weight of the formulation.

Non-pH-dependent polymers that can be used for coating multiparticulates or tablets (matrix or immediate release) include: cellulose esters, cellulose acetate, cellulose acetate butyrate, ethylcellulose, Eudragit® RS and Eudragit® RL poly(ethyl acrylate-co-methyl methacrylate-cotrimethylammonioethyl methacrylate chloride), Eudragit® NE 30 D or Eudragit NM 30 D poly(ethyl acrylate-co-methyl methacrylate), ethyl acrylate methyl methacrylate copolymer, polyvinyl acetate, and combinations thereof.

In addition, the following enteric compounds can be used in a coating to provide a delay in the release profile: Eudragit® FS 30 D (poly(methyl acrylate-co-methyl methacrylate-co-methacrylic acid)), Eudragit® L and Eudragit® S (poly(methacrylic acid-co-methyl methacrylate)), Eudragit® L 100-55 (methacrylic acid-ethyl acrylate copolymer), Eudragit® L 30 D-55 (methacrylic acid-ethyl acrylate copolymer dispersion), hydroxypropyl methylcellulose acetate succinate, hydroxypropyl methylcellulose phthalate, cellulose acetate phthalate, shellac, zein and combinations thereof.

These polymers may be used to prepare a variety of MR systems:

A) Matrix systems, wherein an active pharmaceutical ingredient (molindone, or molindone and an additional active); at least one release controlling polymer and at least one pharmaceutically acceptable excipient are homogeneously intermixed to form a matrix. Hydrophilic and hydrophobic polymers listed above may be used to prepare these molindone-containing matrices. These matrices may be presented in the form of matrix tablets, matrix multiparticulates, or in a form of a layer coated onto a substrate. Processes that may be used to produce the matrix formulations include roller compaction granulation, direct compression of mini-tablets, holt melt granulation, wet granulation with extrusion and spheronization, hot melt extrusion, spray drying and lyophilization.

Matrix tablet formulations are capable of providing a single drug release or multiple drug release profiles. Matrix tablet technologies that are capable of providing multiple release profiles include multiple layer tablets (e.g., bilayer or tri-layer tablets), tablet within a tablet technology, encapsulated mini-tablets or a tablet of compressed controlled release pellets.

Potentially, the matrix formulation may be additionally provided with coating or a membrane to further modify the release. In one variation of the embodiment, this membrane may be a semi-permeable rate-controlling membrane comprising a water insoluble, pharmaceutically acceptable polymer. Suitable water insoluble polymers include, for example, cellulose esters, cellulose ethers and cellulose ester ethers. Examples of such polymers include cellulose acylate, cellulose ethyl ether, cellulose diacylate, cellulose triacylate, cellulose acetate, cellulose diacetate, cellulose triacetate, mono-, di- and tricellulose alkyls, mono-, di- and tricellulose aroyls and the like. One or more orifices may be drilled in the membrane. One example of such formulation is presented in the Example 8.

B) Drug-layered systems that comprise an inert core and at least one drug-containing layer coated onto this core. The drug containing layer(s) may be further coated with a layer of a release controlling polymer selected from those listed above. If the drug-containing layer of the drug-layered system does not contain any release-controlling polymers and is of an immediate release, then the release controlling coating is necessary for achieving the MR profiles of the current invention. In the cases when drug-containing layer is an XR matrix layer described above, the release controlling coating is optional and allows for additional modification of the release profile. For example, it may be used to modulate the release (slow initially, faster later; or fast initially, slower later), or to provide a delay in the release. In particular, non-pH-dependent polymers that can be used for coating multiparticulates or tablets (matrix or immediate release) include: cellulose esters, cellulose acetate, cellulose acetate butyrate, ethylcellulose, Eudragit® RS and Eudragit® RL poly(ethyl acrylate-co-methyl methacrylate-cotrimethylammonioethyl methacrylate chloride), Eudragit® NE 30 D or Eudragit NM 30 D poly(ethyl acrylate-co-methyl methacrylate), ethyl acrylate methyl methacrylate copolymer, polyvinyl acetate, and combinations thereof.

In addition, the following enteric compounds can be used in a coating to provide a delay in the release profile: Eudragit® FS 30 D (poly(methyl acrylate-co-methyl methacrylate-co-methacrylic acid)), Eudragit® L and Eudragit® S (poly(methacrylic acid-co-methyl methacrylate)), Eudragit® L 100-55 (methacrylic acid-ethyl acrylate copolymer), Eudragit® L 30 D-55 (methacrylic acid-ethyl acrylate copolymer dispersion), hydroxypropyl methylcellulose acetate succinate, hydroxypropyl methylcellulose phthalate, cellulose acetate phthalate, shellac, zein, and combinations thereof.

Without putting any limitations thereon, the formulations of this embodiment may be exemplified by the following variations that provide different modified pharmacokinetic (PK) profiles for molindone:

Mixed particles in a capsule, compressed tablet or any other dosage form where IR particles are mixed with DR coated XR particles (IR/DR-XR). The IR particles provide the initial release of the therapeutic agent followed by delayed and extended release from the DR coated XR particles. (IR/DR-XR mixed population of particles)

A single population of particles in a capsule, compressed tablet or any other dosage form where the particle incorporates an IR core coated with at least one XR coat, which is coated with DR coat that is subsequently drug layered. The outer drug layer provides the initial release of the therapeutic agent followed by delayed and extended release from the remainder of the particle. (IR/DR-XR single population of particles)

Mixed particles in a capsule, compressed tablet or any other dosage form where a fast-releasing XR particle is mixed with one or more slower releasing XR particles. The fast XR (XR-f) provides the initial release of the therapeutic agent followed by release from the slow-releasing XR particles (XR-f/XR-s mixed population of particles).

A single population of particles in a capsule, compressed tablet or any other dosage form where the particle incorporates IR core coated with a DR coat which is then coated with a drug layer that is subsequently coated with an XR coat to produce a fast XR layer. The fast XR outer layer provides the initial release of the therapeutic agent followed by delayed release from the DR core. (XR-f/DR single population of particles)

A DR coated XR tablet coated with an IR drug layer

A bi-layer tablet with one layer containing the drug in XR form and a $2^{nd}$ layer containing the drug in an IR form A bi-layer tablet with one layer containing the drug in XR form and a $2^{nd}$ layer containing the drug in an DR form a DR coated matrix tablet providing a DR/XR profile.

To optimize stability of molindone in a matrix system, the preferred methods for formulation and processing would be dry (non-aqueous) methods such as direct compression of a dry powder blend, compression of a roller compacted granulation, compression of a holt melt granulation or a hot melt extrudate. The compressible intermediates (i.e., the dry powder blend, roller compacted granulation, hot melt granulation etc.) can be formulated to be rate controlling in nature (i.e., comprise a drug release rate-controlling excipient(s)) or be mixed with release rate controlling excipient(s) prior to tablet compression. Additionally, wet granulations can be manufactured, dried and sized for compression into matrix tablets. Stabilization techniques, such as using acidic pH media, for the drug substance would be required unless non-aqueous media are employed in the wet granulation process. Additionally, in accordance with the nature of this invention, low moisture content excipients and excipients that by their chemical nature create an acidic environment in the matrix are preferably used. The acidic environment promoted by these excipients can also act to promote the solubility of the drug substance which can be desired in a modified release matrix system formulated to deliver drug in the less acidic regions of the gastrointestinal tract.

Processes useful for producing drug-layered systems include solution or dry powder drug layering onto inert substrates (e.g. sugar or microcrystalline cellulose spheres). As mentioned above, due to the chemical instability of molindone the preferred methods for drug layered systems would be the non-aqueous methods (i.e., dry powder drug layering and methods that can process with non-aqueous media). If the method is to include an aqueous solution in the process (e.g., drug layering), stabilization techniques such as using acidic pH aqueous media may be employed. Additionally, it is preferred to use low moisture content excipients and excipients that by their chemical nature create an acidic environment. The combination of these properties in the excipients can result in a synergistic stabilizing action. The acidic environment promoted by these excipients can also act to promote the solubility of the drug substance which can be desired in a modified release drug-layered system formulated to deliver drug in the less acidic regions of the gastrointestinal tract.

(C) The osmotic release systems.

In a further embodiment of this invention, an XR molindone preparation in the form of an osmotic tablet is provided, wherein the drug release rate is determined by the rate of water permeation into the tablet core through a semi-permeable rate-controlling membrane coating.

For stability of molindone in an osmotic tablet formulation the preferred methods for core tablet formulation and processing would be dry methods such as direct compression of a dry powder blend, compression of a roller compacted granulation, compression of a holt melt granulation or a hot melt extrudate. Additionally, fluid bed granulation processes can be used when stabilization techniques for the drug substance are employed such as using acidic pH granulation media or non-aqueous granulation media. It is preferred to use low moisture content excipients and excipients that by their chemical nature create an acidic environment in the core tablet of the osmotic dosage form. The acidic environment promoted by these excipients can also act promote the solubility of the drug substance which can be a desired attribute when the osmotic tablet formulation is to deliver drug in the less acidic regions of the gastrointestinal tract.

For the preparation of the osmotic tablet, molindone is mixed with osmotic agent(s), tableting aides such as diluents and lubricants, and other commonly used excipients. The mixture is tableted either by direct compression or granulation followed by compression. Tablets are then coated with a semi-permeable rate-controlling membrane.

The semipermeable rate-controlling membrane, which surrounds the drug-containing core, comprises a water insoluble, pharmaceutically acceptable polymer. Suitable water insoluble polymers include, for example, cellulose esters, cellulose ethers and cellulose ester ethers. Examples of such polymers include cellulose acylate, cellulose ethyl ether, cellulose diacylate, cellulose triacylate, cellulose acetate, cellulose diacetate, cellulose triacetate, mono-, di- and tricellulose alkyls, mono-, di- and tricellulose aroyls, and combinations thereof.

The semi-permeable rate-controlling membrane is applied on the tablets using standard coating techniques such as spraying, dipping, casting, coating solvent evaporation, molding or compression coating. An orifice is drilled on the tablet coat using laser tablet drilling system or other mechanical means to allow the release of drug from the core. The osmotic agents used for the practice of the current invention are well known in the art and include non-swellable compounds represented by, but not limited to, polyols; carbohydrates including monosaccharides, oligosaccharides, polysaccharides and sugar alcohols; salts; acids and hydrophilic polymers. For example, osmotic agents may be selected from mannitol, maltrin, xylitol, maltitol, lactitol, isomalt, sorbitol, arabitol, erythritol, ribitol, insositol, lactose, glucose, sucrose, raffinose, fructose, dextran, glycine, urea, citric acid, tartaric acid, sodium chloride, potassium chloride, magnesium chloride, disodium hydrogen phosphate, sodium phosphate, potassium phosphate, sodium sulfate, lithium sulfate, magnesium sulfate, magnesium succinate, polyethylene glycol, maltodextrin, cyclodextrins and derivatives, non-swelling block polymers of PEO and PPO, polyols, polyethylene glycols, cellulose ethers, and combinations thereof. Osmotic agents that are acidic by nature may have multiple functions in the formulations of the present invention acting simultaneously as stabilizers. Alternatively, they may provide synergistic action with additional stabilizers.

Osmotic tablets can be formulated as a single or as a multiple layer core. In one embodiment, the osmotic tablet comprises a bilayer core, wherein one layer comprises agents to modulate drug release, such as a solubilizer, that are released in a sustained manner, and the second layer comprises the drug and potentially other agents to modulate drug release. Stabilizers listed above may be contained in at least one layer of the osmotic formulation.

An overcoat of drug can be applied to the osmotic tablet following functional coating to provide an immediate release component to the dosage form. Alternatively, the osmotic tablet may be coated with an enteric polymer on top of the semipermeable rate-controlling membrane providing a DR/XR profile. A non-limiting example of the osmotic formulations of the current invention is presented in the Example 13.

The embodiments listed above are just non-limiting examples of the MR stable formulations of molindone resulting in a product that maintains therapeutic level of the drug in the body from 4 to 24 hours.

Molindone used in the practice of the current invention may be in the form of a single (−) enantiomer, or in the form of a single (+) enantiomer, or in the form of a racemic mixture, or in the form of a non-racemic mixture of enantiomers with various amounts of (−) and (+) enantiomers. In one embodiment, the amount of an (−) enantiomer in the mixture is from 0% to 90% by weight of the active pharmaceutical ingredient. In another embodiment, the amount of (−) enantiomer is from 0% to 75% by weight of the active pharmaceutical ingredient. In a further embodiment, it is from 0% to 50% by weight of the active pharmaceutical ingredient. In a yet further embodiment, it is from 0% to 25% by weight of the active pharmaceutical ingredient.

The techniques for the enantiomer separation are known to those skilled in the art and include chromatographic techniques using enantio-selective stationary phase, capillary electrophoresis, and liquid-liquid extraction techniques. A particular enantiomer can also be produced directly from the synthetic reaction for the manufacture of molindone.

In one embodiment of the invention, an (−) enantiomer of molindone is used for the treatment of CNS disorders including but not limited to impulsive aggression, aggression, or other conduct disorder.

In the other embodiment of the invention, an (+) enantiomer of molindone is used for the treatment of CNS disorders including but not limited to impulsive aggression, aggression, or other conduct disorder.

In the further embodiment of the invention, the use of a mixture of (−) and (+) enantiomers in various ratios in the treatment of CNS disorders, including but not limited to impulsive aggression, aggression, or other conduct disorder.

The formulations of the present invention contain from 0.1 mg to 200 mg of molindone. In one embodiment, the formulations contain from 3 mg to 150 mg of the active.

In one additional embodiment, formulations of molindone as disclosed above may comprise an additional active pharmaceutical ingredient selected from mazindol, viloxazine, amphetamines, methylphenidate and other drugs known in the art for the treatment of ADHD. In one variation of this embodiment, the additional active is viloxazine, which may be incorporated into the formulation in amount of from 0.1 mg to 800 mg. In another variation of this embodiment, the additional active is mazindol, which may be incorporated into the formulation in the amounts of from 0.1 mg to 20 mg.

The invention is further illustrated by, though in no way limited to, the following examples.

EXAMPLES

Example 1 pH-Dependent Stability of Molindone Hydrochloride

Molindone exhibits pH dependent solution state stability. The drug substance is more stable at acidic pH conditions. A stability evaluation at 37° C. in phosphate buffer systems at pH 6.0, pH 6.8 and pH 7.5 (i.e., typical media pH conditions for drug release testing) demonstrated that there was 3% loss at pH 6.0, 6.4% loss at pH 6.8 and 7.5% loss at pH 7.5 following a 24 hour exposure period.

Examples 2-5 below refer to the IR formulations of molindone.

Example 2

Immediate Release Molindone Capsules

The component and composition for molindone hydrochloride capsules, 1.67 mg, 3.33 mg, 5.0 mg, and 6.67 mg are in the Table 1:

TABLE 1

| | Immediate Release Molindone Capsules | | | |
|---|---|---|---|---|
| Component [a] | Example 2a | Example 2b | Example 2c | Example 2d |
| Dose | 1.67 mg | 3.33 mg | 5.0 mg | 6.67 mg |
| Molindone Hydrochloride | 152 g | 302.7 g | 454.5 g | 606.4 g |
| Lactose Anhydrous | 18,884 g | 18,733.3 g | 18,581.5 g | 18429.6 g |
| Eudragit L100 | 764 g | 764.0 g | 764.0 g | 764.0 g |
| Magnesium Stearate | 200 g | 200 g | 200 g | 200 g |
| Hard Vegetable Capsules, size 3 Natural [a] | 4,545 g | 4,545 g | 4,545 g | 4,545 g |
| Total | 24,545 g | 24,545 g | 24,545 g | 24,545 g |

[a] The target fill weight is 220 mg for all four strengths
[b] The theoretical average capsule weight 50 mg.

The final moisture content in these formulations was calculated to be 1.6% w/w.

The following stability summaries refer to the formulations of 2a and 2d. The lack of significant NPP (non-parent peak) formation and the stable molindone content at the accelerated stability storage condition of 40° C./75% RH through 2 months indicate a stable formulation.

TABLE 2

Stability Summary for Molindone Hydrochloride Capsule of the Example 2a

| Test | Initial | 1 month (40° C./ 75% RH) | 2 month (40° C./ 75% RH) |
|---|---|---|---|
| Average Content* (% label claim) | 98.2, 98.9 (98.6) | 96.9, 97.6 (97.3) | 95.3, 96.6 (96.0) |
| Non-Parent Peaks† (% label claim) | | | |
| RRT 0.71-0.73 | 0.06, 0.06 | <0.05, <0.05 | <0.05, <0.05 |
| RRT 0.81-0.82 | ND, ND | 0.07, 0.07 | 0.07, 0.07 |
| Total non-parent peak/Sample | 0.1, 0.1 (0.1) | 0.1, 0.1 (0.1) | 0.1, 0.0 (0.1) |

*Average values are provided in parenthesis ( ).
†RRT indicates relative retention time of individual non-parent peaks; ND indicates a non-parent peak was not detected in this sample preparation.
NA: not applicable.

TABLE 3

Stability Summary for Molindone Hydrochloride Capsule of the Example 2d

| Test | Initial | 1 month (40° C./ 75% RH) | 2 month (40° C./ 75% RH) |
|---|---|---|---|
| Average Content* (% label claim) | 98.2, 97.7 (98.0) | 97.6, 97.7 (97.7) | 98.0, 97.8 (97.9) |
| Non-Parent Peaks† (% label claim) | | | |
| RRT 0.81-0.82 | ND, ND | 0.05, 0.05 | 0.06, <0.05 |
| Total non-parent peak/Sample | 0.0, 0.0 (0.0) | 0.1, 0.1 (0.1) | 0.1, 0.0 (0.1) |

*Average values are provided in parenthesis ( ).
†RRT indicates relative retention time of individual non-parent peaks; ND indicates a non-parent peak was not detected in this sample preparation.
NA: not applicable.

Example 3

Immediate Release Capsule Formulation Exhibiting Poor Stability (Higher Moisture Content, No Stabilizer)

For comparison purposes, an IR capsule formulation exhibiting poor stability due to the high moisture content is exemplified in Table 4 below:

TABLE 4

Immediate Release Formulation with Poor Stability

| Component | Example 3a Amount (mg) | Example 3b Amount (mg) |
|---|---|---|
| Molindone hydrochloride | 0.33 | 6.67 |
| Microcrystalline cellulose | 118.47 | 112.13 |
| Magnesium stearate | 1.20 | 1.20 |
| Hard gelatin capsule, size 3 white opaque | 48.00 | 48.00 |
| Total | 168.00 | 168.00 |

The final moisture content in this formulation was calculated to be 7% w/w.

TABLE 5

Stability Summary for Molindone Hydrochloride Capsules (3a), 0.33 mg, SS07QQ

| Test | Initial | 1 month (25° C./ 60% RH) | 1 month (30° C./ 65% RH) | 1 month (40° C./ 75% RH) |
|---|---|---|---|---|
| Average Content* (% label claim) | 100.0, 99.2 (99.6) | 98.3, 96.2 (97.3) | 98.1, 99.6 (98.9) | 94.8, 94.4 (94.6) |
| Non-Parent Peaks† (% label claim) | | | | |
| RRT 0.14 | <0.05, ND | ND, ND | ND, ND | ND, ND |
| RRT 0.14-0.15 | <0.05, <0.05 | <0.05, <0.05 | 0.06, 0.06 | <0.05, <0.05 |
| RRT 0.37-0.38 | <0.05, <0.05 | ND, <0.05 | <0.05, <0.05 | ND, <0.05 |
| RRT 0.54-0.56 | <0.05, <0.05 | <0.05, <0.05 | <0.05, <0.05 | <0.05, <0.05 |
| RRT 0.58-0.59 | 0.08, 0.10 | 0.05, 0.05 | <0.05, <0.05 | <0.05, 0.06 |
| RRT 0.64-0.65 | <0.05, <0.05 | <0.05, <0.05 | <0.05, <0.05 | <0.05, <0.05 |
| RRT 0.67-0.68 | ND, ND | ND, ND | <0.05, <0.05 | <0.05, <0.05 |
| RRT 0.72-0.75 | 0.29, 0.30 | 0.35, 0.34 | 0.40, 0.39 | 2.09, 2.07 |
| RRT 0.80 | <0.05, <0.05 | <0.05, <0.05 | <0.05, <0.05 | <0.05, <0.05 |
| RRT 0.96 | ND, ND | <0.05, <0.05 | ND, ND | <0.05, <0.05 |
| RRT 1.33-1.36 | 0.10, 0.10 | 0.09, 0.09 | 0.10, 0.09 | 0.09, 0.09 |
| Total non-parent peaks | 0.5, 0.5 | 0.5, 0.5 | 0.6, 0.5 | 2.2, 2.2 |
| Dissolution | 93, 96, 102, 102, 90, 94 | 103, 103, 99, 103, 101, 100 | NA | 95, 101, 90, 90, 92, 93 |

*Average values are provided in parenthesis ( ).
†RRT indicates relative retention time of individual non-parent peaks; ND indicates a non-parent peak was not detected in this sample preparation.
NA: not applicable.

TABLE 6

Stability Summary for Molindone Hydrochloride Capsules (3b), 6.67 mg, SS07RR

| Test | Initial | 1 month (25° C./ 60% RH) | 1 month (30° C./ 65% RH) | 1 month (40° C./ 75% RH) |
|---|---|---|---|---|
| Average Content* (% label claim) | 95.8, 99.1 (97.5) | 96.9, 98.2 (97.6) | 97.3, 97.3 (97.3) | 97.3, 93.0 (95.2) |
| Non-Parent Peaks† (% label claim) | | | | |
| RRT 0.38 | ND, ND | ND, ND | <0.05, <0.05 | ND, ND |
| RRT 0.54-0.56 | ND, <0.05 | ND, ND | <0.05, <0.05 | ND, <0.05 |
| RRT 0.58-0.59 | <0.05, <0.05 | <0.05, <0.05 | <0.05, <0.05 | <0.05, <0.05 |
| RRT 0.72-0.75 | 0.06, 0.06 | 0.07, 0.07 | 0.07, 0.07 | 0.37, 0.35 |
| RRT 0.80 | ND, <0.05 | ND, <0.05 | 0.06, <0.05 | ND, <0.05 |
| RRT 2.11 | ND, <0.05 | ND, ND | ND, ND | ND, ND |
| Total non-parent peaks | 0.1, 0.1 | 0.1, 0.1 | 0.1, 0.1 | 0.4, 0.4 |
| Dissolution | 102, 103, 101, 102, 101, 102 | 102, 105, 100, 105, 104, 100 | NA | 107, 102, 99, 99, 101, 92 |

*Average values are provided in parenthesis ( ).
†RRT indicates relative retention time of individual non-parent peaks; ND indicates a non-parent peak was not detected in this sample preparation.
NA: not applicable.

Example 4

Preparation of a Stabilizing Excipient

This Example demonstrates the concept of acidifying the bulking/diluent agent in a capsule or tablet formulation to create a more stable pH environment for the active drug substance.

The following ingredients were used:

| | |
|---|---|
| Lactose Anhydrous | 1940 g |
| Eudragit L100 | 60 g |
| Isopropyl Alcohol | 462 g |
| Deionized Water | 28 g |

The manufacturing process is described briefly as follows and any formulation and process variations are within the scope of this invention.

Mix the isopropyl alcohol and deionized water

Add 60 g of Eudragit L100 and stir till it dissolves in the solution completely.

Spray Eudragit L100 solution onto Lactose anhydrous in a fluidized bed (GCPG-1, Glatt Air Technique) using a set of appropriate processing conditions.

Eudragit L100 pretreated lactose can be used as an excipient for molindone hydrochloride formulations.

Example 5

Batch Formula for Immediate Release Molindone HCl Capsules, 3 mg

The batch formula for a representative batch of Molindone HCl capsules, 3 mg is provided in Table 7 below.

TABLE 7

Batch Formula Molindone HCl Capsules, 3 mg

| Component | Usage (g) |
|---|---|
| Molindone Hydrochloride | 16.57 |
| Anhydrous Lactose, NF | 927.02 |
| Eudragit L 100 | 46.41 |
| Magnesium Stearate, NF | 10.00 |
| Hard Vegetable Capsules, Size 3, Natural | 275.00 |
| Total (g) | 1275.0 |

The final moisture content in this formulation was calculated to be 1.3% w/w.

Examples 6-15 refer to the sustained release formulations of molindone.

Example 6

Tablet B—Molindone HCl Extended Release Tablets, 9 mg

The batch formula for a representative batch of Tablet B—Molindone HCl Extended Release Tablets, 9 mg is provided in Table 8 below.

TABLE 8

Tablet B, Molindone HCl Extended Release Tablets 9 mg

| Component | Usage (g) |
|---|---|
| Molindone Hydrochloride | 112.5 |
| Hypromellose (Type 2208), USP | 750.0 |
| Anhydrous Lactose, NF | 1462.5 |
| Eudragit L 100 | 125.0 |
| Colloidal Silicon Dioxide, NF | 25.0 |
| Magnesium Stearate, NF | 25.0 |
| Total (g) | 2500.0 |

The final moisture content in this formulation was calculated to be 0.8% w/w.

Example 7

Tablet C—Molindone HCl Extended Release, 9 mg

The batch formula for a representative batch of Tablet C—Molindone HCl Extended Release, 9 mg is provided in Table 9 below.

TABLE 9

Batch Formula Tablet C - Molindone HCl Extended ReleaseTablets, 9 mg

| Component | Usage (g) |
|---|---|
| Molindone Hydrochloride | 112.5 |
| Hypromellose (Type 2208), USP | 1500.0 |
| Anhydrous Lactose, NF | 337.5 |
| Glyceryl Behenate, NF | 375.0 |
| Eudragit L 100 | 125.0 |
| Colloidal Silicon Dioxide, NF | 25.0 |
| Magnesium Stearate, NF | 25.0 |
| Total (g) | 2500.0 |

The final moisture content in this formulation was calculated to be 1.3% w/w

Example 8

Tablet D—Molindone HCl Extended Release Tablets, 9 mg

The manufacturing process for Tablet D involved the manufacture of the core tablet (Tablet A) followed by the coating of Tablet A with a semipermeable rate-controlling membrane and then laser drilled with one orifice to produce Tablet D.

The batch formula for a representative batch of core Tablet A—Molindone HCl Extended Release, 9 mg is provided in Table 10 below.

TABLE 10

Batch Formula for Core Tablet A - Molindone HCl Extended Release 9 mg

| Component | Usage (g) |
|---|---|
| Molindone Hydrochloride | 112.5 |
| Hypromellose (Type 2208), USP | 750.0 |
| Anhydrous Lactose, NF | 1462.5 |
| Eudragit L 100 | 125.0 |
| Colloidal Silicon Dioxide, NF | 25.0 |
| Magnesium Stearate, NF | 25.0 |
| Total (g) | 2500.0 |

The batch formula for a representative batch of Tablet D—Molindone HCl Extended Release 9 mg is provided in Table 11 below:

TABLE 11

Batch Formula for Tablet D Molindone HCl Extended Release, 9 mg

| Component | Usage (g) |
|---|---|
| SPN-810M Tablet A (Molindone HCl Extended Release Tablets), 9 mg | 2000 |
| Cellulose Acetate, NF | 38.78 |
| Polyethylene Glycol (3350), NF | 1.85 |
| Sterile Water for Irrigation, USP | NA [a] |
| Acetone, NF | NA [a] |
| Total (g) | 2040.63 |

[a] Removed during processing.

The final moisture content in this formulation was calculated to be 0.8% w/w

Stability Data Summaries for Example 6, 7, 8

TABLE 12

Stability Data for Example 6, Tablet B

| Test | Initial | 6 months (25° C./ 60% RH) | 6 months (30° C./ 65% RH) | 6 months (40° C./ 75% RH) |
|---|---|---|---|---|
| Average Content* (% label claim) | 101.4, 100.6 (101.0) | 99.3, 99.1 (99.2) | 99.8, 100.1 (100.0) | 98.5, 99.9 (99.2) |
| Non-Parent Peaks[†] (% label claim) | | | | |
| RRT 0.54-0.56 | ND, ND | ND, ND | <0.06, <0.06 | ND, ND |
| RRT 0.72-0.75 | ND, ND | <0.06, <0.06 | <0.06, <0.06 | 0.20, 0.20 |
| Total NPP | 0.0, 0.0 | 0.0, 0.0 | 0.0, 0.0 | 0.2, 0.2 |

*Average values are provided in parenthesis ( ).
[†]NPP indicates non-parent peaks, RRT indicates relative retention time of individual non-parent peaks; ND indicates a non-parent peak was not detected in this sample preparation, Limit of Quantitation for NPPs is 0.06%.

TABLE 13

Stability data for Example 7, Tablet C

| Test | Initial | 6 months (25° C./ 60% RH) | 6 months (30° C./ 65% RH) | 6 months (40° C./ 75% RH) |
|---|---|---|---|---|
| Average Content* (% label claim) | 97.9, 97.6 (97.8) | 98.3, 98.8 (98.6) | 99.6, 99.1 (99.4) | 98.0, 98.3 (98.2) |
| Non-Parent Peaks[†] (% label claim) | | | | |
| RRT 0.54-0.56 | ND, ND | ND, ND | <0.06, <0.06 | ND, ND |
| RRT 0.72-0.75 | ND, ND | <0.06, <0.06 | <0.06, <0.06 | 0.17, 0.17 |
| Total NPP | 0.0, 0.0 | 0.0, 0.0 | 0.0, 0.0 | 0.2, 0.2 |

| Test | 12 months (25° C./ 60% RH) | 12 months (30° C./ 65% RH) | 18 months (25° C./ 60% RH) |
|---|---|---|---|
| Average Content* (% label claim) | 99.2, 97.8 (98.5) | 96.0, 97.9 (97.0) | 97.0, 96.9 (97.0) |
| Non-Parent Peaks[††] (% label claim) | | | |
| RRT 0.58 | <0.05, <0.05 | <0.05, <0.05 | ND, <0.05 |
| RRT 0.72 | <0.05, <0.05 | <0.05, <0.05 | ND, ND |
| RRT 0.75 | <0.05, <0.05 | 0.08, 0.08 | <0.05, <0.05 |

TABLE 13-continued

Stability data for Example 7, Tablet C

| RRT 0.79-0.80 | <0.05, <0.05 | <0.05, <0.05 | ND, ND |
|---|---|---|---|
| Total NPP | 0.0, 0.0 | 0.1, 0.1 | 0.0, 0.0 |

*Average values are provided in parenthesis ( ).
[†]NPP indicates non-parent peaks, RRT indicates relative retention time of individual non-parent peaks; ND indicates a non-parent peak was not detected in this sample preparation, Limit of Quantitation for NPPs is 0.06%.
[††]NPP indicates non-parent peaks, RRT indicates relative retention time of individual non-parent peaks; ND indicates a non-parent peak was not detected in this sample preparation, Limit of Quantitation for NPPs is 0.05%.

TABLE 14

Stability data for Example 8, Tablet D

| Test | Initial | 6 months (25° C./ 60% RH) | 6 months (30° C./ 65% RH) | 6 months (40° C./ 75% RH) |
|---|---|---|---|---|
| Average Content* (% label claim) | 100.3, 99.5 (99.9) | 101.1, 101.5 (101.3) | 100.8, 100.9 (100.9) | 100.9, 99.6 (100.3) |
| Non-Parent Peaks[†] (% label claim) | | | | |
| RRT 0.54-0.56 | ND, ND | ND, ND | <0.06, <0.06 | ND, ND |
| RRT 0.72-0.75 | ND, ND | <0.06, <0.06 | 0.07, 0.07 | 0.28, 0.28 |
| Total NPP | 0.0, 0.0 | 0.0, 0.0 | 0.1, 0.1 | 0.3, 0.3 |

| Test | 12 months (25° C./ 60% RH) | 12 months (30° C./ 65% RH) | 18 months (25° C./ 60% RH) |
|---|---|---|---|
| Average Content* (% label claim) | 100.0, 100.1 (100.1) | 100.9, 100.4 (100.7) | 98.8, 99.1 (99.0) |
| Non-Parent Peaks[††] (% label claim) | | | |
| RRT 0.58 | <0.05, <0.05 | <0.05, <0.05 | <0.05, <0.05 |
| RRT 0.72 | ND, ND | ND, ND | ND, ND |
| RRT 0.75-0.76 | <0.05, 0.05 | 0.10, 0.10 | 0.06, 0.06 |
| RRT 0.79-0.80 | ND, ND | ND, ND | ND, ND |
| Total NPP | 0.0, 0.1 | 0.1, 0.1 | 0.1, 0.1 |

Average values are provided in parenthesis ( ).
[†]NPP indicates non-parent peaks, RRT indicates relative retention time of individual non-parent peaks; ND indicates a non-parent peak was not detected in this sample preparation, Limit of Quantitation for NPPs is 0.06%.
[††]NPP indicates non-parent peaks, RRT indicates relative retention time of individual non-parent peaks; ND indicates a non-parent peak was not detected in this sample preparation, Limit of Quantitation for NPPs is 0.05%.

Example 9

Pharmacokinetic Profiles for Single Dose Administration of Extended Release Formulations of Examples 6-8

The pharmacokinetic profiles of a single dose of the three molindone XR formulations of Examples 6-8 were evaluated in comparison with the pharmacokinetic profile of the molindone IR formulation of Example 5 administered orally in three divided doses. The study was conducted in healthy adult human volunteers. The results of the study are represented in FIG. 3.

Example 10

Matrix Tablet with Two Stabilizers

A matrix tablet comprising two stabilizers (Eudragit L100 and Carbopol 71G) was prepared (Table 15). Stability data for this tablet are presented in Table 16.

TABLE 15

Matrix Tablet with Two Stabilizers

| Component | Usage (% w/w) | Amount (g) |
|---|---|---|
| Molindone Hydrochloride | 5 | 25.00 |
| Hypromellose (Type 2208) USP | 30 | 150.00 |
| Eudragit L 100 | 5 | 25.00 |
| Avicel PH 112 | 48 | 240.00 |
| Carbopol 71G | 10 | 50.00 |
| Cab-O-Sil M5P | 1 | 5.00 |
| Mg Stearate | 1 | 5.00 |
| Total | 100 | 500.00 |

TABLE 16

Stability data for a matrix tablet with two stabilizers

| Test | Initial | 1 month (25° C./60% RH) | 1 month (40° C./75% RH) | 5 months (25° C./60% RH) | 5 months (40° C./75% RH) |
|---|---|---|---|---|---|
| Average Content* (% label claim) | 95.1, 95.5 (95.3) | 98.8, 99.1 (99.0) | 98.8, 98.0 (98.4) | 97.2, 97.1 (97.2) | 97.3, 93.0 (95.2) |
| Non-Parent Peaks† (% label claim) | | | | | |
| RRT 0.54-0.56 | 0.03, 0.02 | 0.03, 0.04 | 0.03, 0.03 | ND, ND | ND, ND |
| RRT 0.72-0.75 | ND, ND | 0.04, 0.04 | 0.07, 0.07 | ND, ND | ND, ND |
| RRT 0.79 | ND, ND | 0.03, 0.03 | 0.03, 0.03 | ND, ND | 0.11, 0.11 |
| Total NPP | 0.0, 0.0 | 0.1, 0.1 | 0.1, 0.1 | 0.0, 0.0 | 0.1, 0.1 |

*Average values are provided in parenthesis ( ).
†NPP indicates non-parent peaks, RRT indicates relative retention time of individual non-parent peaks; ND indicates a non-parent peak was not detected in this sample preparation The final moisture content in this formulation was calculated to be 1.8% w/w.

Example 11

Bilayer Tablet: IR/XR

The IR formulation powder blend of Example 5, equivalent to a 1.8 mg dose of molindone hydrochloride (108 mg), and the XR formulation of Example 6 or Example 7, equivalent to a 7.2 mg dose (160 mg), are compressed into a bilayer tablet using a conventional bilayer tablet press (Kilian S250-SZ tablet press) producing a MR tablet having an IR component and an XR component.

Example 12

Multiparticulate: Extended Release Mini-Tablets

The formulation of core Tablet A in Example 8 is compressed into mini-tablets on a Piccola Riva tablet press using 2 mm D-tooling at a target tablet weight of 10 mg. The compressed 10 mg mini-tablets are coated with a moisture barrier coating system (e.g., Aquarius® MG, Ashland Aqualon Functional Ingredients) to a weight gain of 3%-5% using conventional pan coating techniques.

The moisture barrier coated mini-tablets are then coated with an extended release polymer solution containing cellulose acetate and PEG 3350 in acetone to the target weight gain to achieve the desired in vitro dissolution profile using conventional pan coating techniques. The cellulose acetate coated mini-tablets are encapsulated (manually or using conventional pellet fill equipment) in the appropriately sized hard vegetable capsules to the fill weight required for the target dose of molindone hydrochloride.

Example 13

Osmotic Tablet of Molindone

TABLE 17

Composition of the osmotic tablet

| Component | Quantity (mg) | % (w/w) |
|---|---|---|
| Molindone Hydrochloride | 85.40 | 4.27 |
| Mannitol, USP | 906.60 | 45.33 |
| Anhydrous Lactose, NF | 781.80 | 39.59 |
| Eudragit L 100 | 94.80 | 4.74 |
| Magnesium Stearate, NF | 19.00 | 0.95 |
| Cellulose Acetate, NF | 82.00 | 4.10 |
| Triethyl Citrate, NF | 20.40 | 1.02 |
| Total | 2000 | 100 |

Powder Blend Manufacturing
1. Anhydrous Lactose, NF, Mannitol USP and Colloidal Silicon Dioxide, NF are simultaneously passed through a 40 mesh sieve into the same container.
2. Approximately one-half of the screened components from Step 1 is charged into an 8 qt V-blender shell.
3. The Molindone Hydrochloride and Eudragit L 100 components are simultaneously screened through a 50 mesh sieve into the same container and then charged to the 8 qt V-blender shell containing the screened components from Step 2.
4. The remaining portion of the screened components from Step 1 is charged to the 8 qt V-blender shell containing the components charged in Step 2 and Step 3.
5. The combined components are blended for 45 minutes at 25 RPM.
6. Magnesium Stearate, NF is passed through a 40 mesh sieve and charged to the 8 qt V-blender shell containing the component mixture from Step 5.

7. The combined components are blended for 9 minutes at 25 RPM.
8. The final powder blend is discharged from the 8 qt V-blender shell and sampled for drug substance assay and non-parent peak testing.

Tablet Compression

1. The final powder blend is compressed on a Piccola Riva tablet press using round 5/16" D-tooling at a target tablet weight of 200 mg.
2. During the tablet compression run tablets are sampled and tested for tablet friability, individual tablet weight, average tablet weight and individual tablet hardness value.
3. Compressed tablets are manually de-dusted and then passed through a metal detector.
4. Following metal detection the bulk tablets are sampled and evaluated for drug release testing, content uniformity, drug substance assay and non-parent peak analysis (for information only).

Tablet Coating and Drilling

1. A solution of Cellulose Acetate, NF and Triethyl Citrate, NF in Acetone, NF is prepared in an appropriately sized stainless steel container using an overhead propeller mixer.
2. The solution prepared in Step 1 is applied to the core tablets using a pan coater with a single nozzle assembly until a coating weight gain in the range of 5.2% (w/w)-5.6% (w/w) is achieved.
3. The coated tablets are laser drilled with one orifice using a mask having an aperture of 60 μm.
4. The drilled bulk tablets are sampled and evaluated for drug release testing and drug substance assay and non-parent peak analysis.

Example 14

Pilot Dose Linearity PK Study in 15 Healthy Subjects

Tablet C 9 mg (Example 7) was dosed to 15 healthy human subjects in a randomized, cross over pilot dose linearity PK study. The doses evaluated were 9 mg (1×9 mg tablet), 18 mg (2×9 mg tablets), 27 mg (3×9 mg tablets) and 36 mg (4×9 mg tablets). The mean PK profiles for the 4 treatments demonstrate that the Tablet C formulation exhibits dose linearity over the dose range of 9 mg to 36 mg (FIG. 7).

Example 15

Pilot Drug Product Proportionality and Linearity PK Study in Healthy Subjects

A pilot PK study was conducted in healthy subjects, evaluating the proportionality and linearity of 4 of the dose strengths of Molindone HCl XR tablet formulations reflected in FIG. 2: 3 mg, 9 mg, 18 mg and 36 mg. On the basis of the dose linearity study results (Example 7), the assumption was that various XR tablet dose strengths with matching in vitro dissolution profiles would exhibit in vivo PK profiles that are dose proportional and linear.

Drug product proportionality study was conducted for a total single dose of 36 mg (i.e., 12×3 mg tablets, 4×9 mg tablets, 2×18 mg tablets and 1×36 mg tablet). The mean PK profiles for the 4 treatments demonstrate that the four tablet formulations exhibit dose proportionality (FIG. 8)

Drug product linearity study was conducted over the dosage strength range of 3 mg to 36 mg (i.e., 1×3 mg tablet, 1×9 mg tablet, 1×18 mg tablet and 1×36 mg tablet). The mean PK profiles for the 4 treatments demonstrate that the four tablet formulations exhibit dose linearity (FIG. 9).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A modified-release formulation comprising molindone as a single active pharmaceutical ingredient,
    (a) at least one release controlling polymer selected from the group consisting of pH-dependent polymers and non-pH-dependent polymers, and
    (b) at least one stabilizer selected from the group consisting of acidifying agents and hydrophobizing agents,
    wherein the total amount of water content in the formulation is not more than 5% by weight of the formulation.

2. The formulation of claim 1 comprising a first molindone-containing component selected from an extended release component and a delayed release component, and a second molindone-containing component selected from an immediate release component, an extended release component and a delayed release component.

3. The formulation of claim 1 for once-a-day administration.

4. The formulation of claim 1 comprising from 0.1 mg to 200 mg of molindone.

5. The formulation of claim 2 comprising a delayed release component comprising from 5% to 95% by weight of the formulation of at least one enteric polymer.

6. The formulation of claim 2 comprising an extended release component comprising from 5% to 95% by weight of the formulation of a non-pH-dependent polymer.

7. The formulation of claim 2 wherein said first component comprises a plurality of the delayed release molindone-containing pellets, and said second component comprises a plurality of the molindone-containing pellets selected from the immediate release pellets, extended release pellets and delayed release pellets.

8. The formulation of claim 7 wherein said delayed release pellets comprise an immediate release core coated with a DR coating.

9. The formulation of claim 7 wherein said delayed release pellets comprise an extended release core coated with a DR coating.

10. The formulation of claim 7 wherein said extended release pellet comprises an immediate release core coated with a layer of a non-pH-dependent polymer.

11. The formulation of claim 7 wherein said extended release pellet comprises an extended release matrix core.

12. The formulation of claim 7 wherein said second component comprises a plurality of delayed release pellets, wherein the first and second components are different from each other.

13. The formulation of claim 2 wherein said first component comprises a plurality of the extended release molindone-containing pellets, and said second component comprises a plurality of the molindone-containing pellets selected from the immediate release pellets and extended release pellets.

14. The formulation of claim 13 wherein both first and second components comprise a plurality of the extended release pellets and components are different from each other.

15. The formulation of claim 2 wherein said first component comprises a molindone-containing core coated with a DR coating, and said second component comprises an IR drug layer or an extended release drug layer coated on top of the DR coating.

16. The formulation of claim 15 wherein said molindone-containing core is an immediate release core.

17. The formulation of claim 15 wherein said molindone-containing core is an extended release core.

18. The formulation of claim 17 wherein said extended release core comprises an immediate release core coated with a coating of the non-pH-dependent polymer.

19. The formulation of claim 17 wherein said extended release core comprises molindone admixed with at least one non-pH-dependent polymer.

20. The formulation of claim 15 wherein said second component further comprises a coating of the non-pH-dependent polymer on top of the IR drug layer.

21. The formulation of claim 15 wherein said extended release drug layer comprises molindone admixed with at least one non-pH-dependent polymer.

22. The formulation of claim 2 wherein the first and second components 1 and 2 are identical.

23. The formulation of claim 1 comprising an osmotic core comprising molindone and at least one pharmaceutically acceptable excipient, and a semipermeable rate-controlling membrane immediately surrounding said core.

24. The formulation of claim 23 additionally comprising a molindone-containing layer on top of the semipermeable membrane.

25. The formulation of claim 24 wherein said molindone-containing layer is an immediate release, extended release or delayed release.

26. The formulation of claim 1 wherein said formulation is stabilized by inclusion of the comprising an acidifying agent as the stabilizer into the formulation.

27. The formulation of claim 26 wherein the acidifying agent is selected from the group consisting of fumaric acid, citric acid, malic acid, tartaric acid, ascorbic acid, edetic acid, aspartic acid, adipic acid, alginic acid, benzoic acid, butandioic acid, erythorbic acid, lactic acid, malic acid, maleic acid, glutamic acid, sorbic acid, succinic acid, hydrochloric acid (dilute) nitric acid (dilute), phosphoric acid (dilute), sulfuric acid (dilute), acacia, aluminum phosphate, aluminum sulfate, ammonium alum, ammonium chloride, carbomers, edetate calcium disodium, edetate disodium, methacrylic acid copolymers, poly(methyl acrylate-comethyl methacrylate-co-methacrylic acid), polycarbophils, polydextrose, potassium alum, potassium phosphate monobasic, sodium metabisulfite, sodium phosphate monobasic, sodium starch glycolate, zinc acetate, zinc sulfate and pharmaceutical grade ion exchange resins.

28. The formulation of claim 1 comprising a hydrophobizing agent as the stabilizer.

29. The formulation of claim 28 wherein said hydrophobizing agent is selected from the group consisting of magnesium stearate, stearic acid, glyceryl behenate, and glyceryl stearate, glyceryl palmitostearate, waxes and hydrogenated vegetable oils.

30. The formulation of claim 1 further comprising at least one pharmaceutically acceptable excipient selected from the group consisting of bulking agents, fillers, lubricants, wetting and solubility enhancing agents and dispersants.

31. The formulation of claim 1 comprising a pH-dependent polymer selected from the group consisting of poly(methyl acrylate-co-methyl methacrylate-co-methacrylic acid), poly(methacrylic acid-co-methyl methacrylate), methacrylic acid-ethyl acrylate copolymer, methacrylic acid-ethyl acrylate copolymer dispersion, hydroxypropyl methylcellulose acetate succinate, hydroxypropyl methylcellulose phthalate, cellulose acetate phthalate, shellac, and zein.

32. The formulation of claim 1 comprising a non-pH-dependent polymer selected from the group consisting of hydroxypropyl cellulose, hypromellose (hydroxypropyl methyl cellulose), methyl cellulose, polyethylene oxide, acacia, carbomer homopolymer type A NF; carbomer homopolymer type B NF, hydroxyethyl cellulose, carrageenan, tragacanth, xanthan gum, povidone, alginic acid and salts thereof, polyvinyl alcohol, carboxymethylcellulose; ethylcellulose, cellulose acetate, cellulose acetate butyrate, poly(ethyl acrylate-co-methyl methacrylate) ethyl acrylate methyl methacrylate copolymer, poly(ethyl acrylate-co-methyl methacrylate-cotrimethylammonioethyl methacrylate chloride), polyvinyl acetate, and cellulose acetate propionate.

33. The formulation of claim 1 wherein molindone is a racemic mixture of (+)-enantiomer and (−)-enantiomer.

34. The formulation of claim 1 wherein molindone is in the form of (+)-enantiomer.

35. The formulation of claim 1 wherein molindone is in the form of (−)-enantiomer.

36. The formulation of claim 1 wherein molindone is in the form of a mixture of (+)- and (−)-enantiomers wherein the amount of the "+"-enantiomer is from 0 to 25%.

37. The formulation of claim 1 wherein molindone is in the form of a mixture of R and S enantiomers wherein the amount of the R-enantiomer is from 0 to 50%.

38. The formulation of claim 1 wherein molindone is in the form of a mixture of (+)- and (−)-enantiomers wherein the amount of the (+)-enantiomer is from 0 to 75%.

39. The formulation of claim 1 wherein molindone is in the form of a mixture of (+)- and (−)-enantiomers wherein the amount of the (+)-enantiomer is from 0 to 90%.

40. The formulation of claim 1 in a dosage form selected from tablets, osmotic tablets, matrix tablets, mini tablets, capsules, beads, granules, powders, caplets, troches, sachets, cachets, pouches, gums, sprinkles, solutions and suspensions.

41. A method of treating impulsive aggression, aggression, or other conduct disorder comprising administering to a subject in need thereof an effective amount of the formulation of claim 1.

42. The method of claim 41, wherein the subject is a human being.

43. The formulation of claim 1 comprising stabilizer and molindone, respectively, in a weight ratio of 0.1:1 to 50:1.

44. The formulation of claim 1 comprising stabilizer and molindone, respectively, in a weight ratio of 0.25:1 to 40:1.

* * * * *